United States Patent [19]

Wilson et al.

[11] 4,039,588

[45] Aug. 2, 1977

[54] HERBICIDAL 4-NITRO-DIPHENYL ETHERS

[75] Inventors: Harold F. Wilson, Jenkintown; Marvin H. Fleischfresser, Warrington, both of Pa.

[73] Assignee: Rohm and Haas Company, Philadelphia, Pa.

[21] Appl. No.: 32,412

[22] Filed: Apr. 27, 1970

Related U.S. Application Data

[63] Continuation-in-part of Ser. No. 828,732, May 28, 1969, abandoned.

[51] Int. Cl. .................................................. C07c 43/28
[52] U.S. Cl. ........................... 260/613 R; 260/612 R; 260/465 F; 260/465 G; 260/577; 260/609 F; 71/105; 71/121; 71/124
[58] Field of Search .................... 260/613 R, 612 R

[56] References Cited

U.S. PATENT DOCUMENTS

| | | | |
|---|---|---|---|
| 2,141,667 | 12/1938 | Petitcolas | 260/613 R |
| 3,080,225 | 3/1963 | Wilson et al. | 260/612 R X |
| 3,401,031 | 9/1968 | Inoue et al. | 260/612 R X |
| 3,417,146 | 12/1968 | Linn et al. | 260/613 R X |
| 3,420,892 | 1/1969 | Martin et al. | 260/613 R X |
| 3,454,392 | 7/1969 | Kato et al. | 260/612 R X |
| 3,506,720 | 4/1970 | Model et al. | 260/613 R |

*Primary Examiner*—Bernard Helfin

[57] ABSTRACT

This invention relates to novel herbicidal compounds of the formula

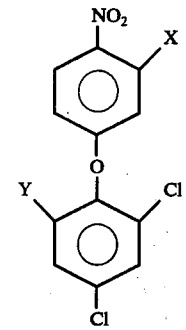

wherein
 X is a $(C_1-C_6)$alkoxy group, a $(C_1-C_4)$alkyl group, an alkoxyalkoxy group, wherein each alkyl moiety has 1 to 4 carbon atoms, a $(C_1-C_4)$alkylamino group, a $(C_1-C_4)$dialkylamino group, a halogen atom, a cyano group, a trifluoromethyl group, a hydroxy group, or a $(C_1-C_4)$ alkylthio group, and
 Y is a hydrogen atom, or a halogen atom, to herbicidal compositions which contain these compounds, and to methods of controlling weeds with the herbicidal compositions.

4 Claims, No Drawings

HERBICIDAL 4-NITRO-DIPHENYL ETHERS

CROSS-REFERENCE TO RELATED APPLICATION

This application is a continuation-in-part of copending U.S. application Ser. No. 828,732, filed on May 28, 1969 and now abandoned.

This invention relates to novel compounds which show activity as herbicides, to novel herbicidal compositions which contain these compounds, and to new methods of controlling weeds with these herbicidal compositions.

Certain diphenyl ethers have been shown to be effective weed control agents. For example, U.S. Pat. No. 3,080,225 of Wilson et al., granted March 5, 1963, discloses the use of 2,4-dichloro-4'-nitrodiphenyl ether, 2,4-dibromo-4'-nitrodiphenyl ether and 3-chloro-4'-nitrodiphenyl ether as herbicides. However, the herbicidal effectiveness of a given diphenyl ether cannot be predicted from an examination of the substituent groups attached to the phenyl rings in the ether, and often quite closely related compounds will have quite different weed control abilities. Various diphenyl ethers may have overlapping or complementary areas of activity or selectivity, and can thus be useful in combination to control a variety of weeds upon application of a single composition. Furthermore, the diphenyl ethers heretofore disclosed as herbicides are not completely effective. An ideal herbicide should give selective weed control, over the full growing season, with a single administration at low rates of application. It should be able to control all common weeds by killing them as the seed, the germinating seed, the seedling, and the growing plant. At the same time, the herbicide should not be phytotoxic to the crops to which it is applied and should decompose or otherwise be dissipated so as not to poison the soil permanently. The known diphenyl ether herbicides fall short of these ideals, and it would thus be desirable to have new herbicides which show even more selective control of undesirable plants among desirable crop plants or which complement the known diphenyl ethers in activity.

Accordingly, it is an object of the invention to provide novel compounds which show activity as weed control agents. Another object of the invention is to provide novel herbicidal compositions comprising any of the novel weed control agents and an agronomically acceptable carrier. A further object of the invention is to provide novel methods of controlling weeds, both in preemergence and in postemergence applications. These and other objects will be apparent from the specification and claims.

In accordance with the present invention, there is provided a new class of novel diphenyl ethers having the formula

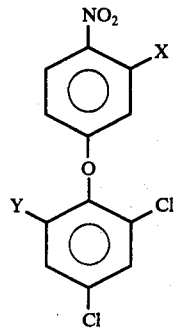

wherein
X is a $(C_1-C_6)$alkoxy group, preferably a $(C_1-C_4)$alkoxy group, a $(C_1-C_4)$alkyl group, an alkoxyalkoxy group, wherein each of the alkyl moieties has 1 to 4 carbon atoms, a $(C_1-C_4)$alkylamino group, a $(C_1-C_4)$ dialkylamino group, a halogen atom, preferably a chlorine or fluorine atom, a cyano group, a trifluoromethyl group, a hydroxy group, a $(C_1-C_4)$alkylthio group, and
Y is a hydrogen atom, a halogen atom, preferably a fluorine atom or a chlorine atom.

The alkyl portion of the alkyl-containing X substitutents can have either a straight- or branched-chain or a cyclic spatial configuration. These novel compounds have been found to show unexpected activity as weed control agents.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the crop plants have emerged and during their growth period.

Among the crops on which the diphenyl ethers of the invention can be advantageously employed are, for example, rice, wheat, cotton, soybeans, peanut, corn, and cole crops, such as cabbage and broccoli.

The diphenyl ethers of the invention are particularly useful as broad spectrum aquatic herbicides, such as for controlling weeds in rice crops. When used in direct-seeded rice crops, the ethers are applied postemergence to both the rice plants and the weeds — that is, they are applied to the plants during early stages of growth and will selectively control growth of the weeds. When used in transplanted rice crops, the ethers can be applied either preemergence or postemergence to the weeds — that is, they can be applied to the transplanted rice plants and their growth medium either before the weed plants are in their early stages of growth. The ethers can be applied to the growth medium either before or after the rice has been transplanted to that medium. For use as selective rice herbicides those diphenyl ethers of the invention in which X is an alkoxy group are preferred.

The diphenyl ethers of the invention can be applied to the soil or to crops in any amount which will give the required control of weeds. A preferred rate of application of the herbicides of the invention is from about 0.5 to about 12 pounds of the diphenyl ether per acre.

A diphenyl ether of the invention can be applied to the growth medium or to plants to be treated either by itself or, as is generally done, as a component in a herbicidal composition or formulation which also comprises an agronomically acceptable carrier. By agronomically acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, the diphenyl ethers can be formulated as wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers 1969 Annual".

The diphenyl ether compounds of this invention can be dissolved in any appropriate solvent. Examples of solvents which are useful in the practice of this invention include alcohols, ketones, aromatic hydrocarbons, dimethylformamide, dioxane, dimethyl sulfoxide, and the like. Mixtures of these solvents can also be used. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates in usually about 10% to 25% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating a solid such as granular fuller's earth, vermiculite, ground corn cobs, seed hulls, including bran or other grain hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formulations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids and Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters 2-methyl-4-chlorophenoxyactic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,6-endoxohexahydrophthalic acid
dimethyl 2,3,5,6-tetrachloroterephthalate
trichloroacetic acid and its salts
2,2-dichloropropionic acid and its salts
2,3-dichloroisobutyric acid and its salts Carbamic Acid Derivatives ethyl N,N-di(n-propyl)thiolcarbamate
propyl N,N-di(n-propyl)thiolcarbamate
ethyl N-ethyl-N-(n-butyl)thiolcarbamate
propyl N-ethyl-N-(n-butyl)thiolcarbamate
2-chloroallyl N,N-diethyldithiocarbamate
N-methyldithiocarbamic acid salts
ethyl 1-hexamethyleneiminecarbothiolate
isopropyl N-phenylcarbamate
isopropyl N-(m-chlorophenyl)carbamate
4-chloro-2-butynyl N-(m-chlorophenyl)carbamate
methyl N-(3,4-dichlorophenyl)carbamate Phenols dinitro-o-(sec-butyl)phenol and its salts
pentachlorophenol and its salts Substituted Ureas 3-(3,4-dichlorophenyl)-1,1-dimethylurea
3-(4-chlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-1-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
dichloral urea Substituted Triazines 2-chloro-4,6-bis(ethylamino)-s-triazine
2-chloro-4-ethylamino-6-isopropylamino-s-triazine
2-chloro-4,6-bis(methoxypropylamino)-s-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropylamino-s-triazine Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether Anilides N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-α,α-dimethylvaleramide Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil Nitriles 2,6-dichlorobenzonitrile
diphenylacetonitrile
3,5-dibromo-4-hydroxybenzonitrile
3,5-diiodo-4-hydroxybenzonitrile Other Organic Herbicides 2-chloro-N,N-diallylacetamide
N-(1,1-dimethyl-2-propynyl)-3,5-dichlorobenzamide
maleic hydrazide
3-amino-1,2,4-triazole
monosodium methanearsonate
disodium methanearsonate
N,N-dimethyl-α,α-diphenylacetamide
N,N-di(n-propyl)-2,6-dinitro-4-trifluoromethylaniline
N,N-di(n-propyl)2,6dinitro-4-methylaniline
N,N-di(n-propyl)-2,6-dinitro-4-methylsulfonylaniline
O-(2,4-dichlorophenyl)-O-methyl-isopropylphosphoramidothioate
4-amino-3,5,6-trichloropicolinic acid
2,3-dichloro-1,4-naphthoquinone
di(methoxythiocarbonyl)disulfide
6,7-dihydrodipyridol[1,2-a:2',1'-c]pyrazidinium salts
1,1'-dimethyl-4,4'-bipyridinium salts
3,4,5,6-tetrahydro-3,5-dimethyl-2-thio-2H-1,3,5-thiadiazine.

When mixtures of herbicides are employed, the relative proportions which are used will depend upon the crop to be treated and the degree of selectivity in weed control which is desired.

The following examples will further illustrate this invention but are not intended to limit it in any way.

The diphenyl ethers of the invention can be prepared by reacting a suitably substituted phenol, or the potassium or sodium salt of the phenol, with a suitably substituted halobenzene, such as chloro- or fluorobenzene, in the presence of an alkaline agent. Examples 1-3 illustrate this method of preparation. The 3'-hydroxydiphenyl ethers can be prepared by the acid-catalyzed dealkylation of a 3'-alkoxy diphenyl ether. This method of preparation is illustrated in Example 4.

EXAMPLE 1

Preparation of 2,4-dichloro-3'-methoxy-4'-nitrodiphenyl ether

A mixture of 48 g. of 5-chloro-2-nitroanisole, 43.2 g. of 2,4-dichlorophenol, and 29.8 g. of potassium fluoride dissolved in 121 g. of sulfolane is heated at 160°–180° C. overnight. The cooled reaction mixture is washed free of sulfolane with water and the residue is distilled to give a fraction with a boiling point of 130°–140° C. (0.3 mm). This fraction is dissolved in hot hexane and on cooling 25 g. (33%) of 2,4-dichloro-3'-methoxy-4'-nitrodiphenyl ether (m.p. 109°–110° C.) is isolated by filtration.

EXAMPLE 2

Preparation of 2,4-dichloro-3'-methyl-4'-nitrodiphenyl ether

Potassium 2,4-dichlorophenate is prepared by dissolving 6.5 g. (0.04 mole) of 2,4-dichlorophenol and 2.6 g. (0.04 mole) of 85% potassium hydroxide in 30 ml. of methanol and removing the solvent under reduced pressure. The solid residue is dissolved in 60 ml. of sulfolane and 6.2 g. (0.04 mole) of 3-methyl-4-nitrofluorobenzene is added. The resulting solution is heated at 85° C. for 3 hours then at 150° C. for 1 hour, cooled, diluted with water and extracted with ether/benzene. The extract is dried and the solvent removed. The residue is dissolved in hot isopropanol and on cooling 8.2 g. (69%) of 2,4-dichloro-3'-methyl-4'-nitrodiphenyl ether (m.p. 72.5°–73.5° C.) separated and is isolated by filtration.

EXAMPLE 3

Preparation of 2-fluoro-4,6-dichloro-3'-methoxy-4'-nitrodiphenyl ether 9.95 g. (0.055 mole) of 2-fluoro-4,6-dichlorophenol is converted to the sodium salt by treatment with 1.35 g. (0.055 mole of oil-free sodium hydride in 130 ml. of diglyme. To this solution is added 9.4 g. (0.055 mole) of 2-nitro-5-fluoroanisole dissolved in 50 ml. of diglyme. After heating under reflux for 3 days, 80 ml. of diglyme is distilled from the reaction mixture and 100 ml. of dimethylsulfoxide is added. The mixture is then heated at 75° C. overnight, then at 95° C. over two nights, and finally at 150° C. overnight. The reaction mixture is diluted with water and extracted with ether. The ether extract is washed with water, dried, and the solvent removed to give 9 g. of oil. This is dissolved in hexane, the solution filtered and the solvent removed to give 6.1 g. of oil. This is chromatographed on 300 g. of 10% deactivated neutral alumina. The product is eluted with 5% benzene in hexane and is recrystallized from pure heptane to give 1.3 g. of 2-fluoro-4,6-dichloro-3'-methoxy-4'-nitrodiphenyl ether, melting 115.5°–117° C.

EXAMPLE 4

Preparation of 2,4-dichloro-3'-hydroxy-4'-nitrodiphenyl ether

A solution of 9.4 g. (0.03 mole) of 2,4-dichloro-3'-methoxy-4'-nitrodiphenyl ether is heated under reflux in 60 ml. of 48% aqueous hydrobromic acid and 18 ml. of acetic acid for 52 hours. The reaction mixture is then cooled, extracted with benzene, and the extract washed with water, dried, and the solvent removed. The residue is chromatographed on 75 g. of silica gel and the product eluted with benzene and recrystallized from benzene/hexane to give 3.5 g. (39%) of 2,4-dichloro-3'-hydroxy-4'-nitrodiphenyl ether, m.p. 74°–75° C.

EXAMPLES 5 to 16

Following the procedures of Examples 1 to 4, the following diphenyl ethers are prepared:
2,4-dichloro-3'-trifluoromethyl-4'-nitrodiphenyl ether
2,4-dichloro-3'-cyano-4'-nitrodiphenyl ether
2,4,3'-trichloro-4'-nitrodiphenyl ether
2,4-dichloro-3'-ethoxy-4'-nitrodiphenyl ether,
2,4-dichloro-3'-dimethylamino-4'-nitrodiphenyl ether,
2,4-dichloro-3'-n-butoxy-4'-nitrodiphenyl ether,
2,4-dichloro-3'-isopropoxy-4'-nitrodiphenyl ether
2,4-dichloro-3'-n-propoxy-4'-nitrodiphenyl ether
2,4-dichloro-3'-isopropylamino-4'-nitrodiphenyl ether
2,4-dichloro-3'-(2-methoxy)ethoxy-4'-nitrodiphenyl ether
2,4-dichloro-3'-methylthio-4'-nitrodiphenyl ether, and
2,4,6-trichloro-3'-methyl-4'-nitrodiphenyl ether.

Table I summarizes the physical properties of the diphenyl ethers of Examples 1 to 16.

TABLE I

DIPHENYL ETHERS - PHYSICAL PROPERTIES

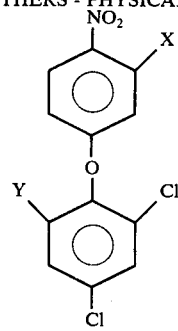

| Example No. | X | Y | m.p. | Analysis | | | | | |
|---|---|---|---|---|---|---|---|---|---|
| | | | | | % C | % H | % N | % Cl | % O | Other |
| 1 | OCH$_3$ | H | 109–110° C. | Found | 49.7 | 3.1 | 4.4 | 22.5 | 20.3 | |
| | | | | theo. | 49.7 | 2.9 | 4.5 | 22.5 | 20.4 | |

TABLE I-continued
DIPHENYL ETHERS - PHYSICAL PROPERTIES

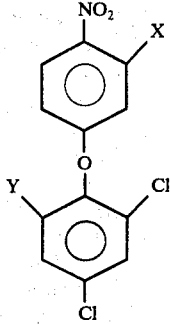

| Example No. | X | Y | m.p. | | | | Analysis | | | |
|---|---|---|---|---|---|---|---|---|---|---|
| 2 | $CH_3$ | H | 72.5–73.5° C. | Found | 52.5 | 3.0 | 4.6 | 23.5 | 15.9 | |
| | | | | theo. | 52.4 | 3.0 | 4.7 | 23.8 | 16.1 | |
| 3 | $OCH_3$ | F | | Found | 46.8 | 2.7 | 3.9 | 21.4 | 19.3 | 5.97 } % F |
| | | | | theo. | 47.0 | 2.4 | 4.2 | 21.4 | 19.3 | 5.7 |
| 4 | OH | H | 74–75° C. | Found | 47.8 | 2.3 | 4.3 | 24.2 | 20.9 | |
| | | | | theo. | 48.0 | 2.3 | 4.7 | 23.6 | 21.3 | |
| 5 | CN | H | 151.5–152.5° C. | Found | 50.5 | 1.9 | 8.7 | 22.8 | 15.5 | |
| | | | | theo. | 50.5 | 1.9 | 9.1 | 22.9 | 15.5 | |
| 6 | Cl | H | 77–78° C. | Found | 45.6 | 2.0 | 4.2 | 33.4 | 15.3 | |
| | | | | theo. | 45.2 | 1.9 | 4.4 | 33.4 | 15.1 | |
| 7 | $OC_2H_5$ | H | 38–38.5° C. | Found | 51.2 | 3.4 | 4.2 | 21.8 | 19.1 | |
| | | | | theo. | 51.2 | 3.4 | 4.3 | 21.6 | 19.5 | |
| 8 | $N(CH_3)_2$ | H | 76–77° C. | Found | 51.0 | 3.8 | 8.3 | 21.3 | 14.3 | |
| | | | | theo. | 51.4 | 3.7 | 8.6 | 21.7 | 14.7 | |
| 9 | $OC_4H_9$-n | H | 49–52° C. | Found | 53.6 | 4.0 | 4.2 | 19.9 | 18.3 | |
| | | | | theo. | 54.0 | 4.2 | 3.9 | 19.9 | 18.0 | |
| 10 | $SCH_3$ | H | 118–120° C. | Found | 47.5 | 2.8 | 4.1 | 21.5 | 14.3 | 9.7 } (% S) |
| | | | | theo. | 47.3 | 2.7 | 4.2 | 21.5 | 14.5 | 9.7 |
| 11 | $CF_3$ | H | 58.5–59.5° C. | Found | 44.5 | 1.6 | 4.0 | 20.0 | — | 16.4 } (% F) |
| | | | | theo. | 44.3 | 1.7 | 4.0 | 20.1 | 13.6 | 16.2 |
| 12 | $CH_3$ | Cl | 111–112.5° C. | Found | 47.2 | 2.5 | 4.1 | 31.5 | 14.2 | |
| | | | | theo. | 47.0 | 2.4 | 4.2 | 32.0 | 14.4 | |
| 13 | i-$C_3H_7O$ | H | 82–83° C. | Found | 52.8 | 3.9 | 4.0 | 20.8 | | |
| | | | | theo. | 52.7 | 3.8 | 4.1 | 20.7 | | |
| 14 | n-$C_3H_7O$ | H | 71–72° C. | Found | 52.7 | 3.8 | 4.0 | 20.7 | | |
| | | | | theo. | 52.7 | 3.8 | 4.1 | 20.7 | | |
| 15 | i-$C_3H_7NH$ | H | 94–95° C. | Found | 52.8 | 4.2 | 8.0 | 20.6 | | |
| | | | | theo. | 52.8 | 4.1 | 8.2 | 20.8 | | |
| 16 | $CH_3OCH_2CH_2O$ | H | 62–64° C. | Found | 50.7 | 3.8 | 3.8 | 19.5 | | |
| | | | | theo. | 50.4 | 3.7 | 3.9 | 19.8 | | |

EXAMPLE 17

Following the procedures of Examples 3 and 4, using 2-fluoro-4,6-dichlorophenyl or 2,4,6-trichlorophenol, fluorine- and chlorine-substituted diphenyl ethers of the invention are prepared. Among the compounds which are prepared by these procedures are:

2-fluoro-4,6-dichloro-3'-methyl-4'-nitrodiphenyl ether
2-fluoro-4,6-dichloro-3'-cyano-4'-nitrodiphenyl ether
2-fluoro-4,6,3'-trichloro-4'-nitrodiphenyl ether
2,4,6-trichloro-3'-ethoxy-4'-nitrodiphenyl ether
2,4,6-trichloro-3'-dimethylamino-4'-nitrodiphenyl ether
2,4,6-trichloro-3'-n-butoxy-4'-nitrodiphenyl ether
2,4,6-trichloro-3'-methylthio-4'-nitrodiphenyl ether
2,4,6-trichloro-3'-hydroxy-4'-nitrodiphenyl ether, and
2,4,6,3'-tetrachloro-4'-nitrodiphenyl ether.

These diphenyl ethers have herbicidal properties.

It should be noted that the diphenyl ethers of the invention can also be named correctly using different systems of nomenclature. For example, the diphenyl ether of Example 1 can also be named as 2,4-dichlorophenyl 3-methoxy-4-nitro-phenyl ether. However, within the specification and claims of this invention the diphenyl ether nomenclature, as exemplified in Examples 1–17, has been followed.

The following examples show the unexpected herbicidal properties of the new diphenyl ethers of the invention, as well as the improved properties which these new compounds show when compared to known diphenyl ether herbicides.

EXAMPLE 18

This example shows the herbicidal activity of diphenyl ethers of the invention towards a number of common weeds. Using the procedure described below, diphenyl ethers were evaluated for control of the following weeds:

crabgrass (*Digitaria spp.*)
foxtail (*Setaria faberii*)
millet (*Setaria italica*)
wheat (*Triticum vulgare*)
ryegrass (*Lolium perenne*)
wild oats (*Avena fatua*)
Sudangrass (*Sorghum sudanesis*)
mustard (*Brassica haber*)
wild carrot (*Daucus carota*)
lambsquarters (*Chenopodium album*)
sorrel (*Rumex spp.*)
curly dock (*Rumex crispus*)
velvetleaf (*Abutilon theophrasti*)
pigweed (*Amaranthus retroflexus*)
bean (*Phaseolus vulgaris*)
flax (*Linum usitatissimum*)
barnyardgrass (*Echinochloa crusgalli*)

Bermudagrass (*Cynodon dactylon*)
downy brome (*Bromus tectorum*)
Johnsongrass (*Sorghum halepense*)
nutsedge (*Cyperus esculentus*)
quackgrass. (*Agropyron repens*)
blindweed (*Convolvulus arvensis*)
cocklebur (*Xanthium pensylvanicum*)
morningglory (*Ipomoea purpurea*)

The following test procedure is employed. Seeds of selected crops and weeds are planted in soil in flats. For preemergence tests, the flats are treated with the test compound immediately after the planting. For postemergence tests, the seeds are allowed to germinate, and after two weeks the flats are treated with the test compound. The compound to be evaluated is sprayed over the flats using a carrier volume equivalent to 50 gallons per acre at the rate of application (pounds per acre, lb/A.) specified in the tables. About two weeks after the application of the test compound, the state of growth of the plants is observed and the phytotoxic effect of the compound is evaluated. Tables II-V give the average percent control achieved by the test compounds in terms of the percent of the plants which are killed by the compounds.

The following diphenyl ethers were evaluated:
(I) 2,4-dichloro-3'-methoxy-4'-nitrodiphenyl ether
(II) 2,4-dichloro-3'-methyl-4'-nitrodiphenyl ether
(III) 2-fluoro-4,6-dichloro-3'-methoxy-4'-nitrodiphenyl ether
(IV) 2,4-dichloro-3'-hydroxy-4'-nitrodiphenyl ether
(V) 2,4-dichloro-3'-cyano-4'-nitrodiphenyl ether
(VI) 2,4,3'-trichloro-4'-nitrodiphenyl ether
(VII) 2,4-dichloro-3'-ethoxy-4'-nitrodiphenyl ether
(VIII) 2,4-dichloro-3'-dimethylamino-4'-nitrodiphenyl ether
(IX) 2,4-dichloro-3'-n-butoxy-4'-nitrodiphenyl ether
(X) 2,4-dichloro-3'-methylthio-4'-nitrodiphenyl ether
(XI) 2,4-dichloro-3'-trifluoromethyl-4'-nitrodiphenyl ether
(XII) 2,4,6-trichloro-3'-methyl-4'-nitrodiphenyl ether
(XIII) 2,4-dichloro-3'-isopropoxy-4'-nitrodiphenyl ether
(XIV) 2,4-dichloro-3'-n-propoxy-4'-nitrodiphenyl ether
(XV) 2,4-dichloro-3'-isopropylamino-4'-nitrodiphenyl ether
(XVI) 2,4-dichloro-3'-(2-methoxy)ethoxy-4'-nitrodiphenyl ether Table II and Table III summarizes the results of these tests.

TABLE II

PREEMERGENCE ACTIVITY (% KILL)

| Compound | lb/A | Barn-yard-grass | Barn-yard-grass | Crab-grass | Downy brome | Fox-tail | John-son-grass | Millet | Nut-sedge | Quack-grass | Rye-grass | Sudan-grass | Wild Oat | Bind-weed | Cockle-bur | Curly dock | Lambs-quar-ters | Morning-glory | Pig-weed | Vel-vet-leaf | Wild carrot | Wild mus-tard | Flax | Sorrel |
|---|---|---|---|---|---|---|---|---|---|---|---|---|---|---|---|---|---|---|---|---|---|---|---|---|
| I | 4 | 100 | — | — | — | — | — | — | — | — | — | — | 70 | — | — | 100 | 100 | — | 100 | 50 | — | 40 | 70 | 100 |
| II | 5 | — | — | 100 | — | — | — | 100 | — | — | 90 | 50 | 30 | 40 | — | 100 | 99 | — | 99 | — | 0 | 0 | 0 | — |
| III | 4 | 0 | — | 80 | 0 | — | — | 100 | 0 | 0 | 90 | 90 | 70 | — | — | 100 | 100 | — | 100 | 20 | — | 40 | 80 | — |
| IV | 5 | 0 | — | 0 | — | — | — | 0 | — | — | 0 | 100 | 0 | — | — | 90 | 90 | 60 | 90 | — | — | 0 | — | — |
| V | 5 | 90 | 100 | 100 | — | 100 | 100 | 100 | — | — | 0 | — | 0 | 0 | — | 0 | 0 | — | 0 | — | 0 | 0 | 50 | — |
| VI | 5 | 100 | 100 | 95 | 30 | — | 90 | — | 0 | 30 | 80 | 20 | 20 | 0 | 30 | 100 | 90 | 0 | 90 | 0 | 0 | 40 | 50 | — |
| VII | 5 | 100 | 90 | 95 | 30 | — | 80 | — | 0 | 50 | 50 | — | 10 | 0 | 0 | 30 | 60 | 0 | 100 | 0 | 0 | 0 | — | — |
| VIII | 5 | 100 | 80 | 40 | 0 | — | 40 | — | 0 | 20 | 40 | — | 0 | 0 | 100 | 70 | 50 | 0 | 100 | 0 | 0 | 0 | — | — |
| IX | 5 | 40 | — | 100 | — | — | — | 100 | — | 0 | 20 | — | 0 | 0 | 0 | 20 | 70 | 0 | 100 | 0 | 0 | 0 | — | — |
| XI | 5 | — | 100 | 99 | 30 | 100 | 99 | — | 0 | 30 | 60 | 60 | 40 | 0 | — | 20 | 100 | — | 100 | 100 | 0 | — | 30 | — |
| XII | 5 | 80 | — | 100 | 20 | 100 | 90 | 100 | 20 | 70 | 50 | — | 0 | 0 | 30 | 100 | 90 | 90 | 100 | 100 | 0 | 50 | — | — |
| XIII | 5 | 80 | — | 100 | 50 | 90 | 50 | — | 10 | 80 | 60 | — | 30 | — | — | 80 | 100 | 20 | 90 | 20 | 70 | 0 | — | — |
| XIV | 5 | 80 | — | 90 | 40 | 40 | 60 | 90 | 20 | 70 | 60 | — | 50 | — | 30 | 90 | — | 20 | 90 | 40 | 20 | 20 | — | — |
| XV | 5 | 40 | — | 90 | 20 | 70 | 20 | 70 | 0 | 70 | 20 | — | 0 | — | 0 | 100 | — | 40 | 100 | 40 | 40 | 0 | — | — |
| XVI | 5 | | | | | | | | | | | | | | | | | | | | | | | |

TABLE III

PREEMERGENCE ACTIVITY (% KILL)

| Compound | lb/A | Barn-yard-grass | Barn-yard-grass | Crab-grass | Downy brome | Fox-tail | John-son-grass | Millet | Nut-sedge | Quack-grass | Rye-grass | Sudan-grass | Wild Oat | Bind-weed | Cockle-bur | Curly dock | Lambs-quar-ters | Morning-glory | Pig-weed | Vel-vet-leaf | Wild carrot | Wild mus-tard | Flax | Wheat |
|---|---|---|---|---|---|---|---|---|---|---|---|---|---|---|---|---|---|---|---|---|---|---|---|---|
| I | 4 | — | — | 50 | — | — | — | 40 | — | — | 40 | 50 | 50 | — | — | 100 | 100 | — | 100 | 90 | 30 | 50 | 100 | 20 |
| II | 5 | 80 | — | 70 | — | — | — | 90 | — | — | 70 | 70 | 60 | — | — | 100 | 100 | — | 100 | — | 0 | 90 | 100 | — |
| III | 4 | — | — | 60 | — | — | — | 70 | — | — | 60 | 70 | 70 | 100 | — | 100 | 100 | — | 100 | 100 | 20 | 60 | 100 | 60 |
| IV | 5 | 70 | 100 | 70 | 20 | 100 | 60 | — | 20 | 30 | 20 | — | 20 | — | 90 | 70 | 70 | 100 | 100 | — | 10 | 20 | — | — |
| V | 5 | 20 | — | 20 | — | — | — | 0 | — | — | 0 | 0 | 0 | — | — | 70 | 70 | — | 90 | — | 90 | 20 | 0 | — |
| VI | 5 | 80 | — | 70 | — | — | — | 100 | — | — | 80 | 60 | 50 | 100 | — | 100 | 100 | 80 | 100 | 100 | 0 | 80 | 100 | — |
| VII | 5 | 100 | 100 | 100 | 80 | 100 | 100 | — | 70 | 100 | 80 | — | 90 | 30 | — | 100 | 100 | 50 | 100 | 100 | 40 | 80 | — | — |
| VIII | 5 | 70 | 100 | 95 | 50 | 100 | 100 | — | 30 | 80 | 50 | — | 60 | 90 | 40 | 100 | 100 | 50 | 100 | 90 | 20 | 40 | — | — |
| IX | 5 | 80 | 100 | 100 | 60 | 100 | 100 | — | 20 | 80 | 40 | — | 30 | 100 | 30 | 90 | 80 | 50 | 100 | 90 | 30 | 60 | — | — |
| X | 5 | — | — | 70 | 40 | 80 | 70 | 70 | 30 | 60 | 30 | 30 | 10 | 60 | — | 100 | 60 | — | 100 | 100 | 10 | 40 | — | 40 |
| XI | 5 | 100 | 100 | 60 | — | 100 | — | — | — | — | — | — | 60 | — | 80 | 100 | 100 | 100 | 100 | 100 | 0 | 60 | 100 | — |
| XII | 5 | 99 | 100 | 100 | 100 | 100 | 100 | — | 50 | 80 | 50 | — | 20 | 90 | 50 | 100 | 100 | 80 | 100 | 100 | 0 | 100 | — | — |
| XIII | 5 | 99 | — | 99 | 20 | 100 | 6 | 100 | 20 | 90 | 50 | — | 40 | 90 | 50 | 100 | 100 | 60 | 100 | 100 | 40 | 90 | — | — |
| XIV | 5 | 95 | — | 80 | 60 | 100 | 70 | 90 | 40 | 80 | 30 | — | 50 | 80 | 60 | 100 | 100 | 60 | 100 | 100 | — | 80 | — | — |
| XV | 5 | 50 | — | 50 | 40 | 90 | 60 | 100 | 30 | 40 | 20 | — | — | 90 | 60 | 100 | 100 | 70 | 100 | 100 | — | 90 | — | — |
| XVI | 5 | 80 | — | 50 | 40 | 90 | 50 | 100 | 30 | 40 | 20 | — | — | 90 | 60 | 100 | 100 | 70 | 100 | 100 | — | 90 | — | — |

EXAMPLE 19

Following the procedures of Example 18, the following diphenyl ethers were evaluated:

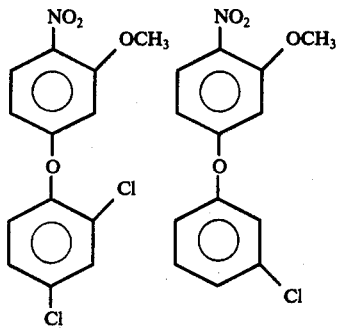

(I)    (A)

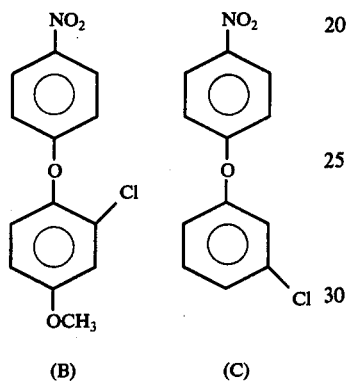

(B)    (C)

Table IV and Table V summarize the results of these tests.

the difference in location of the methoxy substituent within the diphenyl ether molecule makes a crucial difference in the herbicidal activity of the compound.

Using the same procedure, a further test was undertaken to compare the herbicidal properties of compound A and compound C. It was found that compound A was completely ineffective in controlling mustard, wild oats, wild carrot, curly dock, and pigweed, while application of compound C resulted in 90% kill of mustard and 100% kill of wild oats, wild carrot, curly dock, and pigweed. Since the only structural difference between compound A and compound C is the methoxy group ortho to the nitro group, the test results indicate that adding a methoxy substituent does not necessarily improve the herbicidal propeties of a diphenyl ether, and can, as in this example, completely negate the herbicidal activity of the diphenyl ether.

EXAMPLE 20

Following the procedures of Example 18, the following diphenyl ethers were evaluated:

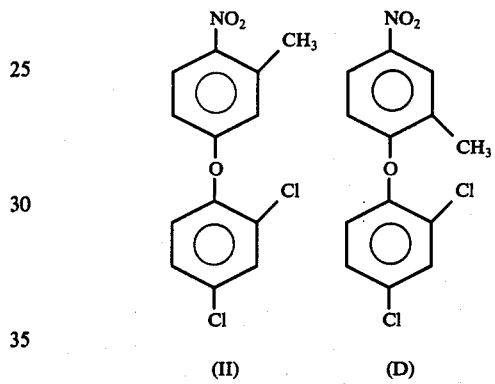

(II)    (D)

TABLE IV

| | | | | | | | | | | | | | | |
|---|---|---|---|---|---|---|---|---|---|---|---|---|---|---|
| | | | | | PREEMERGENCE APPLICATIONS (% KILL) | | | | | | | | | |
| Compound | lb/A | Millet | Wheat | Ryegrass | Wild oats | Sudangrass | Mustard | Wild carrot | Lambsquarters | Sorrel | Curly Dock | Velvetleaf | Pigweed | Flax | Crabgrass |
| I | 4 | 100 | 0 | 90 | 70 | 50 | 40 | 0 | 100 | 100 | 100 | 50 | 100 | 70 | — |
| A | 5 | 0 | 0 | 0 | 0 | 0 | 0 | 0 | 0 | 0 | 0 | 0 | 0 | 0 | — |
| B | 4 | 0 | 0 | 0 | 0 | 0 | 0 | 0 | 0 | — | 0 | 0 | 0 | 0 | — |

TABLE V

| | | | | | | | | | | | | | | |
|---|---|---|---|---|---|---|---|---|---|---|---|---|---|---|
| | | | | | POSTEMERGENCE APPLICATIONS (% KILL) | | | | | | | | | |
| Compound | lb/A | Millet | Wheat | Ryegrass | Wild oats | Sudangrass | Mustard | Wild carrot | Lambsquarters | Sorrel | Curly Dock | Velvetleaf | Pigweed | Flax | Crabgrass |
| I | 4 | 40 | 20 | 40 | 50 | 50 | 50 | 30 | 100 | — | 100 | 90 | 100 | 100 | 50 |
| A | 5 | 30 | 10 | 0 | 0 | 10 | 50 | 0 | 50 | — | 0 | 30 | 50 | 30 | 20 |
| B | 4 | 40 | 10 | 20 | 20 | 10 | 70 | 0 | 70 | — | 90 | 90 | 40 | 40 | 20 |

This data indicates the unexpected superiority of a diphenyl ether of the invention over related diphenyl ethers which also contain a methoxy substituent. Thus, Table VI summarizes the results of these tests.

TABLE VI

| Compound | lb/A | Barn-yard-grass | Crab-grass | Downy brome | Fox-tail | John-son-grass | Nut-sedge | Quack-grass | Rye-grass | Wild oat | Yellow Millet | Bind-weed | Cockle-bur | Curly dock | Lambs-quar-ters | Morning-glory | Pig-weed | Smart-weed | Vel-vet-leaf | Wild carrot | Wild mus-tard |
|---|---|---|---|---|---|---|---|---|---|---|---|---|---|---|---|---|---|---|---|---|---|
| \multicolumn{22}{c}{PREEMERGENCE ACTIVITY (% KILL)} |
| II | 5 | 95 | 100 | 90 | 100 | 80 | 40 | 90 | 90 | 60 | 100 | — | 0 | 100 | — | 20 | 100 | 100 | 40 | 20 | 40 |
| D | 5 | 0 | 0 | 0 | 0 | 0 | 0 | 0 | 0 | 0 | 0 | — | 0 | 0 | — | 40 | 0 | 0 | 20 | 0 | 0 |
| \multicolumn{22}{c}{POSTEMERGENCE ACTIVITY (% KILL)} |
| II | 5 | 90 | 100 | 70 | 100 | 95 | 40 | 90 | 60 | 70 | 100 | 100 | 40 | 100 | 100 | 95 | 100 | 100 | 100 | — | 80 |
| D | 5 | 0 | 0 | 0 | 50 | 0 | 0 | 20 | 0 | 0 | 50 | 0 | 0 | 40 | 40 | 20 | 30 | 50 | 20 | — | 0 |

This data shows the high herbicial activity of 2,4-dichloro-3'-methyl-4'-nitrodiphenyl ether, one of the diphenyl ethers of the invention, and the very low herbicidal activity of its position isomer 2,4-dichloro-2'-methyl-4'-nitrodiphenyl ether. Thus, when a methyl group is introduced into the nitro-containing phenyl compounds at 50 gallons per acre with the belt sprayer. After being sprayed the trays were put into a metal tray which was filled with water to the surface of the soil. Observations of injury were made two weeks after spraying.

Tables VII–IX summarize the results of these tests.

TABLE VII
WEED CONTROL AND RICE INJURY IN PADDY TEST (% KILL - AVERAGES OF TWO EXPERIMENTS)

| | | POSTEMERGENCE | | | | | | | | PREEMERGENCE | | | |
| | | 14 Days Old at Treatment lb./A | | | | 7 Days Old at Treatment lb./A | | | | lb./A | | | |
| PLANT | COMPOUND | 1/2 | 1 | 2 | 4 | 1/2 | 1 | 2 | 4 | 1/2 | 1 | 2 | 4 |
| --- | --- | --- | --- | --- | --- | --- | --- | --- | --- | --- | --- | --- | --- |
| Rice | E | 10 | 15 | 30 | 40 | 20 | 40 | 70 | 90 | 40 | 50 | 80 | 90 |
| | I | 5 | 15 | 15 | 20 | 5 | 25 | 40 | 60 | 65 | 88 | 98 | 98 |
| | III | 10 | 15 | 15 | 30 | 25 | 50 | 85 | 90 | 88 | 95 | 100 | 100 |
| Barnyardgrass | E | 30 | 40 | 65 | 70 | 60 | 75 | 98 | 100 | 30 | 70 | 85 | 95 |
| | I | 25 | 45 | 65 | 80 | 88 | 98 | 100 | 100 | 90 | 95 | 100 | 100 |
| | III | 50 | 80 | 90 | 100 | 100 | 100 | 100 | 100 | 100 | 100 | 100 | 100 |
| Ducksalad | E | — | 30 | 80 | 95 | — | — | — | — | 100 | 100 | 100 | 100 |
| | I | 20 | 50 | 100 | 100 | — | — | — | — | 100 | 100 | 100 | 100 |
| | III | 70 | 80 | 100 | 100 | — | — | — | — | 100 | 100 | 100 | 100 |
| Sprangletop | E | 50 | 80 | 95 | 100 | — | — | — | — | 100 | 100 | 100 | 100 |
| | I | 65 | 98 | 100 | 100 | — | — | — | — | 90 | 100 | 100 | 100 |
| | III | 85 | 100 | 100 | 100 | — | — | — | — | 100 | 100 | 100 | 100 | ring, the position at which it is placed makes an unexpectedly crucial difference in the herbicidal activity of the compound.

EXAMPLE 21

This example shows the relative herbicidal activity of diphenyl ethers of the invention (compound I and compound III) and a related known effective herbicide (compound E) in applications to rice (Oryza sativa) crops, and to three of the most troublesome weeds which intrude in rice crops — barnyardgrass (Echinochloa crusgalli), ducksalad (Heteranthera limosa), and sprangletop (Leptochloa imbricata). The following diphenyl ethers were evaluated:

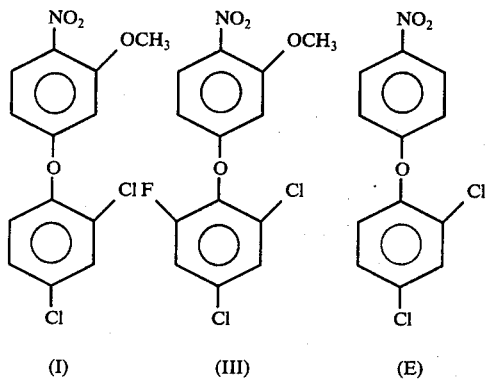

(I)  (III)  (E)

Paddy Test

Plants in three-inch deep pots which are 2 weeks old and 1 week old for postemergence applications and newly planted for preemergence applications were put into a 22-inch square metal pan which was then filled with water to 3 inches above the soil surface of the pots. Compounds were dissolved in 100 ml. of 50% acetone and poured over the water surface. Observations were made two weeks after applications.

Spray applications

Trays containing plants 2 weeks old for postemergence applications and newly planted for preemergence applications were sprayed with acetone solutions of the

TABLE VIII

| | | Postemergence spray applications (% kill) | | | | | |
| | | rice | | | barnyardgrass | | |
| compound | (lb./A) | 1 | 2 | 4 | 1 | 2 | 4 |
| --- | --- | --- | --- | --- | --- | --- | --- |
| I | | 45 | 61 | 54 | 83 | 83 | 88 |
| E | | 48 | 65 | 63 | 61 | 75 | 82 |

TABLE IX

| | | Preemergence spray applications (% kill) | | | | | | | | |
| | | rice | | | | | barnyardgrass | | | |
| compound | (lb./A) | 1/2 | 1 | 2 | 3 | 4 | 1/2 | 1 | 2 | 3 | 4 |
| --- | --- | --- | --- | --- | --- | --- | --- | --- | --- | --- | --- |
| I | | 25 | 12 | 22 | 25 | 30 | 70 | 62 | 90 | 80 | 95 |
| E | | 25 | 5 | 28 | 10 | 30 | 40 | 42 | 80 | 80 | 90 |

In postemergence applications in the paddy test, Compound I is consistently safer than Compound E on rice and more effective than Compound E in controlling barnyardgrass, ducksalad, and sprangletop. In postemergence spray applications, Compound I is generally safer than Compound E on rice with greater effectiveness on barnyardgrass. In preemergeence applications in the paddy test, Compound I is more active than Compound E, and in preemergence spray applications, Compound I is as safe as Compound E on rice and more effective than Compound E on barnyardgrass. Compound III is more active than Compound I in all applications. This data indicates that Compound I and Compound III have definite advantages over Compound E when applied to rice crops.

EXAMPLE 22

This example shows the usefulness of the diphenyl ethers of the invention as selective rice herbicides. Following the procedures of Example 21, the diphenyl ethers of the invention were herbicidally evaluated in a paddy test. To demonstrate the usefulness of these compounds in rice, their phytotoxicity towards rice and their herbicidal activity against barnyardgrass (Echinochloa crusgalli), sprangletop (Leptochloa imbricata), and redstem (Ammania coccinea), three common weeds in rice crops, in various stages of growth has been tabulated in Table X (compound numbers correspond to those in Example 18).

TABLE X

Rates of Weed Control and Rice Injury from Diphenylethers in Paddy Tests (% kill)

| Species | Compound | (lb/A) | Postemergence 14 Days Old at Treatment | | | | | Postemergence 7 Days Old at Treatment | | | | | Preemergence | | | | |
|---|---|---|---|---|---|---|---|---|---|---|---|---|---|---|---|---|---|
| | | | 1/4 | 1/2 | 1 | 2 | 4 | 1/4 | 1/2 | 1 | 2 | 4 | 1/4 | 1/2 | 1 | 2 | 4 |
| Rice | I | | 20 | 40 | 70 | 80 | 20 | 100 | 100 | 100 | 100 | 100 | 95 | 100 | 100 | 100 | 100 |
| | II | | — | — | 90 | 90 | 80 | — | — | 100 | 100 | 100 | — | — | 100 | 100 | 90 |
| | IV | | — | — | — | 0 | — | — | — | 90 | — | — | — | — | — | 90 | — |
| | V | | — | — | — | — | 0 | — | — | — | — | 0 | — | — | — | — | 0 |
| | VI | | — | — | 60 | 80 | 70 | — | — | 100 | 100 | 90 | — | — | 90 | 100 | 90 |
| | VII | | 80 | 95 | 100 | 100 | — | 100 | 100 | 100 | 100 | — | 100 | 100 | 100 | 100 | — |
| | VIII | | — | — | 0 | 30 | — | — | — | 90 | 100 | — | — | — | 50 | 100 | — |
| | IX | | — | — | 0 | 20 | — | — | — | 90 | 100 | — | — | — | 80 | 100 | — |
| | X | | — | — | 0 | 20 | — | — | — | 90 | 100 | — | — | — | 100 | 100 | — |
| | XI | | — | — | — | — | 10 | — | — | — | — | 40 | — | — | — | — | 80 |
| | XII | | — | — | 60 | 70 | 40 | — | — | 100 | 100 | 100 | — | — | 100 | 100 | 100 |
| | XIII | | 20 | 20 | 40 | — | — | 95 | 100 | 100 | — | — | 80 | 100 | 100 | — | — |
| | XIV | | — | 30 | 30 | 50 | 60 | — | 100 | 100 | 100 | 100 | — | 100 | 100 | 100 | 100 |
| | XV | | — | 0 | 10 | 30 | 40 | — | 90 | 100 | 100 | 100 | — | 100 | 100 | 100 | 100 |
| | XVI | | — | 10 | 30 | 40 | 40 | — | 80 | 95 | 80 | 100 | — | 90 | 100 | 100 | 100 |
| Barnyardgrass | I | | 90 | 95 | 90 | 100 | 100 | 100 | 100 | 100 | 100 | 100 | 90 | 95 | 100 | 100 | 100 |
| | II | | — | — | 90 | 100 | 100 | — | — | 100 | 100 | 100 | — | — | 100 | 100 | 100 |
| | IV | | — | — | — | 40 | — | — | — | — | 80 | — | — | — | — | 90 | — |
| | V | | — | — | — | — | 0 | — | — | — | — | 0 | — | — | — | — | 0 |
| | VI | | — | — | 90 | 100 | 90 | — | — | 100 | 100 | 100 | — | — | 90 | 100 | 95 |
| Barnyardgrass | VII | | 100 | 100 | 100 | 100 | — | 100 | 100 | 100 | 100 | — | 100 | 100 | 100 | 100 | — |
| | VIII | | — | — | 10 | 100 | — | — | — | 90 | 100 | — | — | — | 70 | 90 | — |
| | IX | | — | — | 20 | 100 | — | — | — | 100 | 100 | — | — | — | 100 | 100 | — |
| | X | | — | — | 20 | 100 | — | — | — | 100 | 100 | — | — | — | 100 | 100 | — |
| | XI | | — | — | — | — | 70 | — | — | — | — | 90 | — | — | — | — | 90 |
| | XII | | — | — | 70 | 100 | 100 | — | — | 100 | 100 | 100 | — | — | 100 | 100 | 100 |
| | XIII | | 90 | 100 | 100 | — | — | 100 | 100 | 100 | — | — | 80 | 95 | 100 | — | — |
| | XIV | | — | 85 | 95 | 100 | 100 | — | 100 | 100 | 100 | 100 | — | 100 | 100 | 100 | 100 |
| | XV | | — | 40 | 70 | 100 | 100 | — | 100 | 100 | 100 | 100 | — | 100 | 100 | 100 | 100 |
| | XVI | | — | 50 | 60 | 70 | 80 | — | 100 | 100 | 100 | 100 | — | 80 | 100 | 100 | 100 |
| Sprangletop | I | | 70 | 80 | 90 | 100 | 100 | | | | | | | | | | |
| | II | | — | — | 80 | 100 | 100 | | | | | | | | | | |
| | IV | | — | — | — | 40 | — | | | | | | | | | | |
| | V | | — | — | — | — | 0 | | | | | | | | | | |
| | VI | | — | — | 60 | 100 | 100 | | | | | | | | | | |
| | VII | | 80 | 90 | 100 | 100 | — | | | | | | | | | | |
| | VIII | | — | — | 30 | 90 | — | | | | | | | | | | |
| | IX | | — | — | 50 | 100 | — | | | | | | | | | | |
| | X | | — | — | 40 | 90 | — | | | | | | | | | | |
| | XI | | — | — | — | — | 90 | | | | | | | | | | |
| | XII | | — | — | 90 | 100 | 100 | | | | | | | | | | |
| | XIII | | 70 | 90 | 100 | — | — | | | | | | | | | | |
| | XIV | | — | — | — | — | — | | | | | | | | | | |
| | XV | | — | — | — | — | — | | | | | | | | | | |
| | XVI | | — | — | — | — | — | | | | | | | | | | |
| Redstem | I | | 100 | 100 | 100 | 100 | 100 | | | | | | | | | | |
| | II | | — | — | 100 | 100 | 100 | | | | | | | | | | |
| | IV | | — | — | — | 100 | — | | | | | | | | | | |
| | V | | — | — | — | — | 80 | | | | | | | | | | |
| | VI | | — | — | 100 | 100 | 100 | | | | | | | | | | |
| | VII | | 100 | 100 | 100 | 100 | — | | | | | | | | | | |
| | VIII | | — | — | 100 | 100 | — | | | | | | | | | | |
| | IX | | — | — | 100 | 100 | — | | | | | | | | | | |
| | X | | — | — | 100 | 100 | — | | | | | | | | | | |
| | XI | | — | — | — | — | 100 | | | | | | | | | | |
| Redstem | XII | | — | — | 100 | 100 | 100 | | | | | | | | | | |
| | XIII | | 100 | 100 | 100 | — | — | | | | | | | | | | |
| | XIV | | — | 100 | 100 | 100 | 100 | | | | | | | | | | |
| | XV | | — | 100 | 100 | 100 | 100 | | | | | | | | | | |
| | XVI | | — | 100 | 100 | 100 | 100 | | | | | | | | | | |

The above data shows the valuable activity of the compounds of the invention when used as postemergence rice herbicides, as well as their usefulness as selective herbicides when applied preemergence as to weeds in transplanted rice.

We claim:

1. A compound of the formula

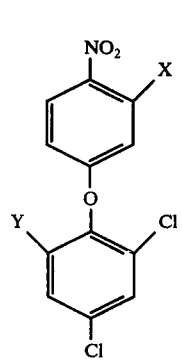

wherein

Y is a hydrogen atom or a halogen atom, and

X is a $(C_1-C_6)$ alkoxy group, an alkoxyalkoxy group, wherein each alkyl moiety has 1 to 4 carbon atoms, a halogen atom, a trifluoromethyl group, or a hydroxy group.

2. A compound according to claim 1 wherein X is a $(C_1-C_4)$ alkoxy group and Y is a hydrogen atom.

3. A compound of the formula

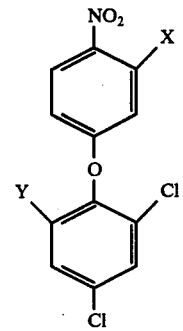

wherein X is a $(C_1-C_4)$ alkoxy group and Y is a hydrogen atom or a halogen atom.

4. A compound of the formula

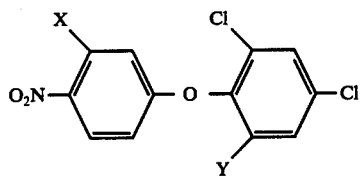

wherein Y is a hydrogen atom or a halogen atom and X is a $(C_1-C_6)$ alkoxy group, a halogen atom or a trifluoromethyl group.

* * * * *